(12) United States Patent
Tockman et al.

(10) Patent No.: US 8,655,458 B2
(45) Date of Patent: Feb. 18, 2014

(54) CONFORMAL ELECTRODES FOR SHAPED MEDICAL DEVICE LEAD BODY SEGMENTS

(75) Inventors: Bruce A. Tockman, Scandia, MN (US); Timothy R. Jackson, Minneapolis, MN (US); Brendan E. Koop, Coon Rapids, MN (US); Lili Liu, Maple Grove, MN (US); Kimberly A. Morris, Minneapolis, MN (US); David J. Parins, Corcoran, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 503 days.

(21) Appl. No.: 12/541,461

(22) Filed: Aug. 14, 2009

(65) Prior Publication Data

US 2010/0063569 A1    Mar. 11, 2010

Related U.S. Application Data

(60) Provisional application No. 61/094,424, filed on Sep. 5, 2008.

(51) Int. Cl.
*A61N 1/05* (2006.01)

(52) U.S. Cl.
USPC ............................ 607/119; 607/126; 607/122

(58) Field of Classification Search
USPC ................................. 607/122, 125, 119, 126
See application file for complete search history.

(56) References Cited

U.S. PATENT DOCUMENTS

| | | | |
|---|---|---|---|
| 4,998,975 A | 3/1991 | Cohen et al. | |
| 5,010,894 A | 4/1991 | Edhag | |
| 5,954,761 A * | 9/1999 | Machek et al. | 607/126 |
| 6,430,425 B1 * | 8/2002 | Bisping | 600/374 |
| 6,438,427 B1 * | 8/2002 | Rexhausen et al. | 607/126 |
| 6,493,590 B1 | 12/2002 | Wessman et al. | |
| 6,584,362 B1 | 6/2003 | Scheiner et al. | |
| 2003/0109914 A1 * | 6/2003 | Westlund et al. | 607/122 |
| 2004/0122496 A1 * | 6/2004 | Zhang et al. | 607/122 |
| 2006/0020331 A1 * | 1/2006 | Bates et al. | 623/1.49 |
| 2006/0241736 A1 | 10/2006 | Haldeman | |
| 2007/0293922 A1 | 12/2007 | Soltis et al. | |
| 2008/0183253 A1 | 7/2008 | Bly | |

FOREIGN PATENT DOCUMENTS

WO    WO 02/18006    3/2002

OTHER PUBLICATIONS

International Search Report and Written Opinion issued in PCT/US2009/053842, mailed Oct. 22, 2009, 13 pages.

* cited by examiner

*Primary Examiner* — Joseph Stoklosa
(74) *Attorney, Agent, or Firm* — Faegre Baker Daniels LLP

(57) ABSTRACT

A medical lead includes a lead body having at least one conductor extending from a proximal end of the lead body to a distal end of the lead body. The proximal end is adapted to be connected to a pulse generator, and the distal end includes a curved portion. One or more electrodes are operatively connected to the at least one conductor and coupled to the curved portion of the lead body. At least a portion of each of the one or more electrodes includes an arrangement of interconnected, spaced-apart elements that are selectively configured to allow the one or more electrodes to conform to contours of the curved portion during and after implantation of the medical lead.

10 Claims, 5 Drawing Sheets

CONFORMAL ELECTRODES FOR SHAPED MEDICAL DEVICE LEAD BODY SEGMENTS

CROSS-REFERENCE TO RELATED APPLICATION

This application claims priority to Provisional Application No. 61/094,424, filed Sep. 5, 2008, which is herein incorporated by reference in its entirety.

TECHNICAL FIELD

The present invention relates to medical device leads. More specifically, the invention relates to conformal electrodes for shaped medical device lead body segments.

BACKGROUND

Cardiac function management systems are used to treat arrhythmias and other abnormal heart conditions. Such systems generally include cardiac leads, which are implanted in or about the heart, for delivering an electrical pulse to the cardiac muscle, for sensing electrical signals produced in the cardiac muscle, or for both delivering and sensing. The lead typically consists of a flexible conductor that may define a central channel or lumen, surrounded by an insulating tube or sheath extending from a connector pin at the proximal end to one or more electrodes along the lead body at the distal end.

Cardiac lead placement may be accomplished by introducing the lead through a major blood vessel and advancing a distal end of the lead to a final destination in or near the heart. For example, for some therapies such as cardiac resynchronization therapy (CRT), the distal end of the lead is advanced through the coronary sinus and coronary veins to the epicardial surface of the heart. To stimulate cardiac tissue, the electrodes should be arranged to contact the myocardial side of the vessel at the final destination. Some leads include a pre-shaped curved or helical portion that forces the electrodes along the lead body against the vessel wall. However, since the orientation of the curved or helical portion of the lead is difficult to predict or control, the likelihood of the electrodes contacting the myocardial side of the vessel is low. One approach to increasing the likelihood of electrode contact is to increase the number of electrodes along the curved or helical portion. However, this increases the complexity of the lead, and the number of electrodes may be limited by available connections to the pulse generator. Another approach to increasing the likelihood of electrode contact is to increase the length of individual electrodes. However, the added electrode length could affect the ability of the distal end of the lead body to retain its curved or helical shape.

SUMMARY

In one aspect, the present invention relates to a medical lead including a lead body having at least one conductor extending from a proximal end of the lead body to a distal end of the lead body. The proximal end is adapted to be connected to a pulse generator, and the distal end includes a curved portion. One or more electrodes are operatively connected to the at least one conductor and coupled to the curved portion of the lead body. At least a portion of each of the one or more electrodes includes an arrangement of interconnected, spaced-apart elements that are selectively configured to allow the one or more electrodes to conform to contours of the curved portion during and after implantation of the medical lead.

In another aspect, a cardiac lead includes a lead body having a proximal end and a distal end including a curved portion. At least one conductor extends through the lead body from the proximal end to the distal end. A connector, which is adapted for connection to a pulse generator, is coupled to the at least one conductor at the proximal end of the lead body. One or more electrodes are operatively connected to the at least one conductor and coupled to the curved portion of the lead body. At least a portion of each of the one or more electrodes includes an arrangement of spaced-apart elements that are configured to allow the one or more electrodes to conform to contours of the curved portion during and after implantation of the cardiac lead.

In a further aspect, an implantable electrode for a cardiac lead includes a tubular member having a plurality of spaced-apart conductive elements arranged in a stent-like structure that is securable to a body of the cardiac lead and operatively connected to a pulse generator for delivery of signals to cardiac tissue.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
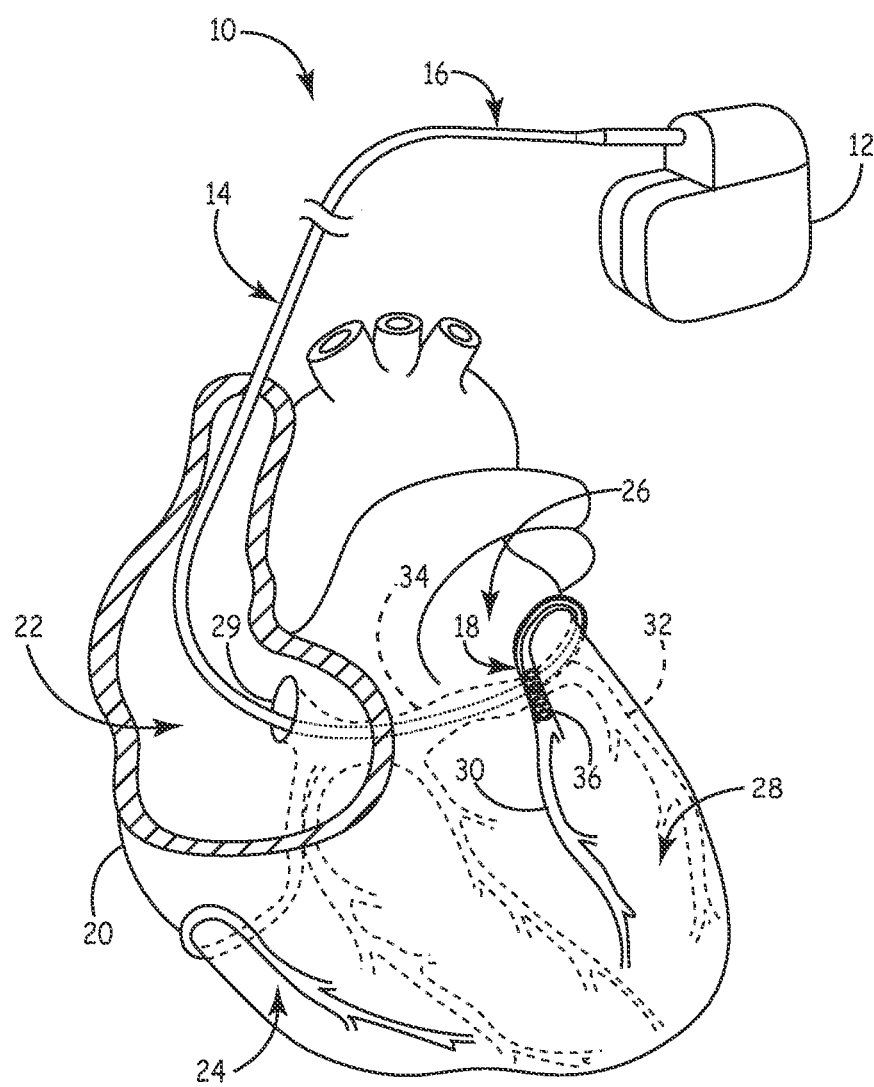
FIG. 1 is a schematic view of a cardiac lead implanted in a cardiac vessel.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management system 10 including a pulse generator 12 coupled to a lead 14 having a proximal end 16 and a distal end 18. As shown in FIG. 1, distal portions of the lead 14 are disposed in a patient's heart 20, which include a right atrium 22, a right ventricle 24, a left atrium 26, and a left ventricle 28. In the embodiment illustrated in FIG. 1, the distal end 18 of the lead 14 is transvenously guided through the right atrium 22, through the coronary sinus ostium 29, and into the anterior coronary vein 30. While distal end 18 is shown in the anterior coronary vein 30, it will be appreciated that distal end 18 may alternatively be guided to other areas of the heart 20, such as other branches 32 of the coronary sinus 34 and great cardiac vein. In accordance with embodiments of the present invention, the distal end 18 has a generally helical portion 36 disposed in anterior coronary vein 30. The illustrated position of lead 14 can be used for sensing or for delivering pacing and/or defibrillation energy to the left side of heart 20, or to treat arrhythmias or other cardiac disorders requiring therapy delivered to the left side of heart 20. Additionally, it will be appreciated that lead 14 can have a different shape (e.g., a sine or s-curve, or a J-curve) and be used to provide treatment in other regions of heart 20 (e.g., the right ventricle) or body.

Figure 2A:
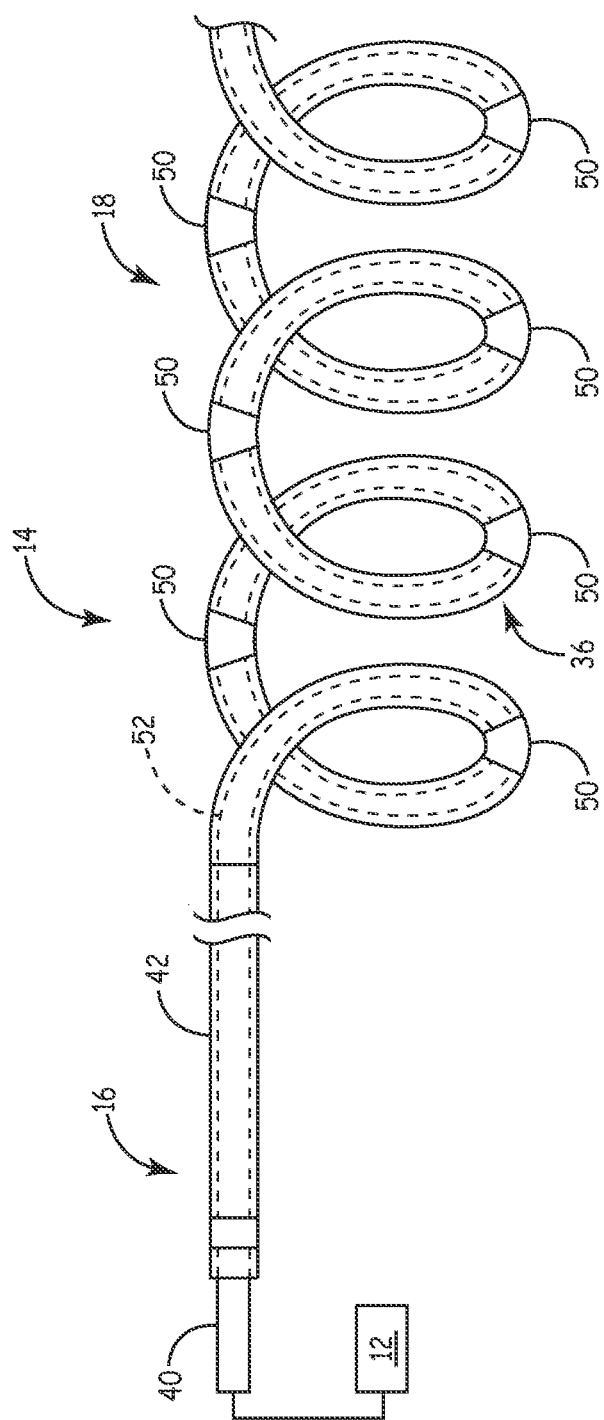
FIG. 2A is a side view of a cardiac lead constructed in accordance with one embodiment of the present invention.

FIG. 2A is a side view of the lead 14 suitable for use in accordance with embodiments of the present invention including a helical distal end 18. The lead 14 includes a connector terminal 40 at proximal end 16 that is coupled to a lead body 42. The lead body 42 extends from the connector terminal 40 to the distal end 18. The connector terminal 40 attaches to the pulse generator 12. The lead body 42 includes a number of electrodes 50 at its distal end 18 which is implanted in a coronary vein. The connector terminal 40 electrically connects the various electrodes and conductors within or on the lead body 42 to the pulse generator 12. The pulse generator 12 contains electronics to sense various pulses of the heart and also produce pulsing signals for delivery to the heart 20. The pulse generator 12 also contains electronics and software to detect certain types of arrhythmias and to correct for them.

The lead body 42 may be a tubing material formed from a biocompatible polymer, such as a silicone rubber, polyurethane, and combinations and/or copolymers thereof. Alternatively, the lead body 42 may be made of a biocompatible material having shape memory characteristics such that it will return to its preformed shape once implanted and a stylet or guidewire is removed. An example of such a material is polyether polyurethane. In addition, the lead body 42 may have portions that have shape memory characteristics, comprising either a shape memory polymer or a shape memory metal. The lead body 42 contains one or more electrical conductors 52 configured to carry current and signals between the pulse generator 12 and the electrodes 50 located at the distal end 18. The electrical conductor(s) 52 is/are made of a highly conductive, highly corrosion-resistant material. As will be appreciated, in some embodiments, at least one of the electrical conductors 52 is in the form of a coil defining a guidewire lumen to slidably receive a guidewire or stylet for delivering the lead 14.

Figure 2B:
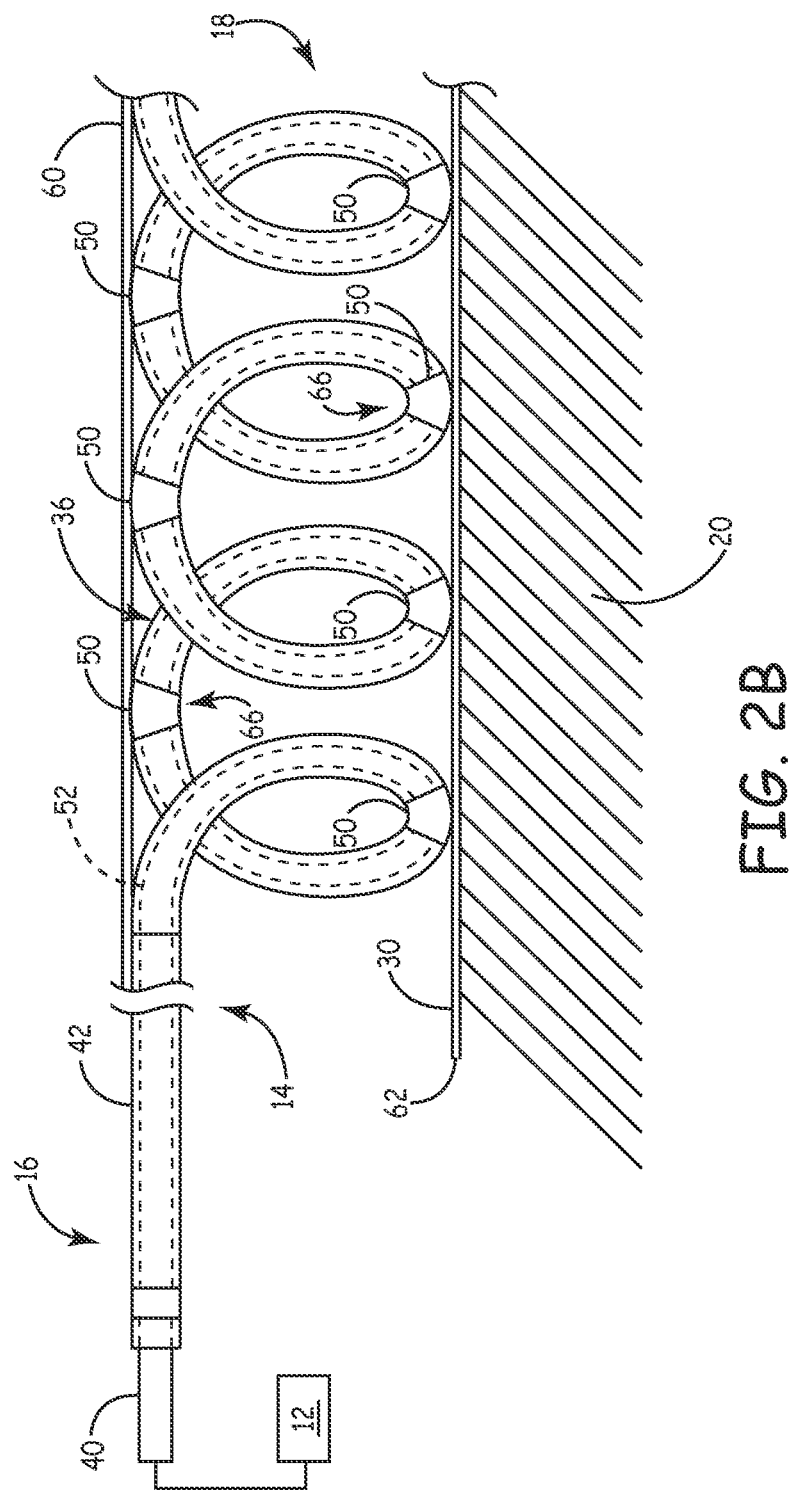
FIG. 2B is a side view of the cardiac lead shown in FIG. 2A disposed in a cardiac vein.

The lead body 42 includes the helical portion 36 at the distal end 18. After implantation, the helical portion 36 may be located in an anterior coronary vein 30, as shown, for example, in FIG. 1. FIG. 2B shows a side view of the distal end 18 of the lead body 42 positioned in the anterior coronary vein 30. The anterior coronary vein 30 includes a free wall 60 and a myocardial wall 62. The free wall 60 is disposed away from the heart 20, and the myocardial wall 62 abuts the heart 20.

The helical portion 36 of the lead body 42 may be made of a biocompatible material having shape memory characteristics such that it will return to its preformed helical shape once implanted and a stylet or guidewire is removed. An example of such a material is polyether polyurethane. In addition, the helical portion 36 may have portions which have shape memory characteristics, comprising either a shape memory polymer or a shape memory metal. In some embodiments, the shape of the helical portion 36 is retained at least in part by the conductor(s) 52 extending within the lead body 42. In some embodiments, the diameter of the helical portion is about 0.50 cm-2.0 cm, and the pitch of the helix ranges from 0.50 cm-2.5 cm.

The helical portion 36 facilitates placement of the electrodes 50 against the myocardial wall 62 of the anterior coronary vein 30 during and/or after implantation. The helical shape of the lead 14 provides large lead/vessel wall area interface to produce reliable, long term stability. When implanted, the helical shape of the lead 14 produces subtle lateral or radial forces between the electrodes 50 and myocardial wall 62, resulting in low pacing thresholds. The helical portion also provides passive fixation by urging the lead body 42 against the vessel wall through frictional forces.

The lead 14 may be any type of lead, such as a tachycardia (tachy) lead, a bradycardia (brady) lead, or a sensing lead. In various embodiments, the electrodes 50 may be masked or otherwise insulated on the inside radius 66 of the helical portion 36. This decreases electrode area and provides an increase in pacing impedance. In some embodiments, the surfaces of electrodes 50 facing the myocardial wall 62 are raised beyond the lead body 42 of the lead. Electrodes designed in this fashion increase the chances of achieving intimate tissue-electrode contact thereby resulting in lower thresholds.

In one embodiment, the lead 14 is delivered to the anterior coronary vein 30 by passing the lead body 42 over a guiding member (e.g., a guidewire) that has a distal end positioned in the anterior coronary vein 30 (not shown). Alternatively, or additionally, the lead 14 may be delivered through a guiding catheter. The lead body 14 passed through the sinus ostium 29 and the coronary sinus 34 to deliver the distal end 18 to the anterior coronary vein 30. During delivery, electrodes 50 conform to the contours of lead body 42. When the distal end 18 reaches the anterior coronary vein 30, the guiding member is withdrawn from the lead body 42, and the helical portion 36 of the distal end 18 returns to its pre-delivery helical configuration. The electrodes 50, which are located along the helical portion 36, conform to the contours of the lead body 42 such that the radius of curvature of the electrodes 50 is substantially the same as the radius of curvature of the turns of the helical portion 36.

In some embodiments, the electrodes 50 are arranged along the distal portion 18 to maximize the likelihood that the electrodes 50 contact the myocardial wall 62 when the helical portion 36 returns to its helical shape. For example, because the electrodes 50 can conform to the contours of the lead body 42, the length of the electrodes 50 along the circumference of turns of the helical portion 36 can be increased. This additional length further increases the likelihood that the electrodes contact the myocardial wall 62 when delivered to the anterior coronary vein 30. In some embodiments, the electrodes 50 cover between about 35% and about 75% of the total length of the helical portion 36. In addition, the electrodes 50 may be selectively spaced apart with respect to each other. Depending on the shape of the lead 14, the electrodes 50 may be disposed on portions of the lead body 42 that are expected to contact the myocardial wall 62. For example, if the lead 14 has an expected known orientation when delivered, the electrodes 50 may be concentrated on a specific side of the lead 14 with reduced spacing between the electrodes 50. As another example, if the lead 14 has an expected random orientation when delivered, the electrodes 50 may be evenly spaced along the lead body 42 to maximize the probability of contact with the myocardial wall 62.

The electrodes 50 may be formed from a tube of conductive material that is machined, cut, or otherwise altered to enhance the flexibility of the tube. In some embodiments, the tube of conductive material is laser cut using techniques generally known in the art. The conductive material may alternatively be mechanically cut or chemically etched. A pattern may be formed into the tube of conductive material to provide a plurality of spaced-apart elements that move with respect to each other to conform to the contours of the lead body 14. For example, the conductive tube may be formed into a stent-like structure. The flexibility of the electrode 50 can be controlled by the pattern and quantity of material removed, for example to provide gradations of flexibility and stiffness to conform to different sections of the lead body 14. The material selected may be highly conductive, highly resistant to corrosion, and biocompatible. In some embodiments, the electrodes 50 are made from a metallic material such as Pt, PtIr, Ti, stainless steel, and alloys thereof. In other embodiments, electrode 50 is made from other types of conductive material, such as Nitinol and MP35N. Once fabricated, the electrodes 50 may be slid onto the helical portion 36 like a sleeve and operatively connected to the conductor(s) 52. Alternatively, the electrodes 50 may be formed over or embedded in the lead body 42, or the electrodes 50 may be formed from a length of wound wire.

Figure 3:
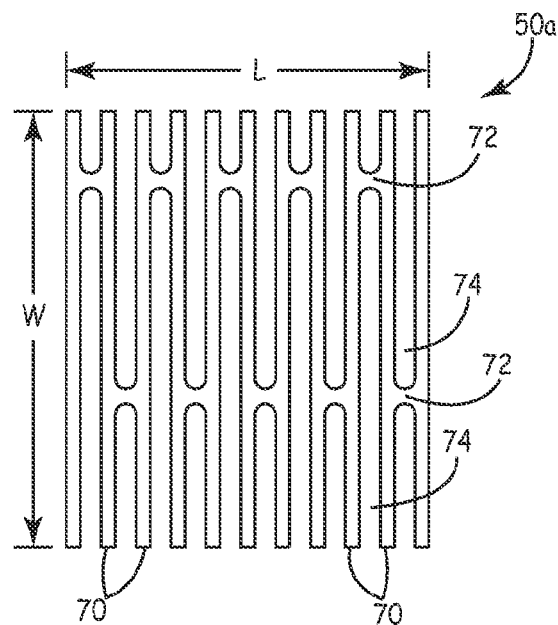
FIG. 3 is a plan view of a conformal electrode according to an embodiment of the present invention.

FIGS. 3-6 are various embodiments of the electrodes 50 that may be formed by laser cutting a tube of conductive material to generate an electrode including spaced-apart elements as described above. FIG. 3 is a plan view of an electrode 50a formed from a conductive tube (e.g., Nitinol) that is cut with a laser to remove material leaving behind the configuration shown. The electrode 50a includes collars 70 having a diameter equal to that of the original tube diameter. Collars 70 are spaced apart along the longitudinal axis or length of the electrode 50. Adjacent collars 70 are connected by struts 72 that extend across the slots or gaps 74 between the collars 70. In some embodiments, the material removed from the conductive tube to form slots or gaps 74 is greater than about 50% of the total material of the conductive tube.

The orientation and location of the collars 70 and the struts 72 relative to the lead body 14 may be controlled to provide preferred operational characteristics for the electrode 50a. For example, the slots or gaps 74 may be formed along the electrode 50a to maximize the surface area around regions of lead 14 that tissue contact is most likely. In addition, removal of material may be controlled to allow the electrode 50a to face in a certain direction, such as the outer diameter of the helical portion 36. This may be accomplished, for example, by removing more material from the inside radius 66 of the helical portion 36 than the outside radius of the helical portion 36. The conductive material may also be cut to orient current vectors generated by the electrode 50a toward the tissue to be stimulated in portions of electrode 50a that tissue contact is most likely. The conductive material may also be cut to focus the current density of the electrode 50a on portions of the electrode 50a most likely to face the myocardial wall 62. Furthermore, solid sections may be interspersed within or located on proximal or distal ends of the electrode 50a to provide attachment areas for the one or more electrical conductors 52.

The pattern of the collars 70 and struts 72 may also be used to affect the mechanical interaction with surrounding tissues. That is, the directional orientation and shape of the collars 70 and struts 72 may be used to prevent dislodgement or movement of the lead 14 relative to the anterior coronary vein 30. The size and quantity of the slots or gaps 74 can also be selected to control tissue adhesion.

The electrode 50a is shown in an unbiased state and has a length L, which extends parallel to the longitudinal axis of the lead body 14, and a width W, which extends across the outer diameter of the electrode 50a. Since the electrode 50a is designed to conform to contours of the lead body 14, the length L of the electrode 50a can be extended to improve the likelihood that the electrode 50a will contact tissue of the heart when implanted. In some embodiments, the length L of the electrode 50a is less than or equal to about 20 mm. One exemplary range for the length L of the electrode 50a is between about 4 mm and about 8 mm. The length L may also be selected to provide a desired amount of coverage of the helical portion 36 by electrodes 50a.

The gaps 74 are laser cut in the tube of conductive material to reduce the total surface area of the electrode 50a. Minimizing the overall surface area of the electrode 50a increases the total impedance of the electrode 50a, which prolongs the battery life of the pulse generator 12. Thus, the design of electrode 50a allows for the minimization of the surface area of the electrode 50a while maximizing the axial length over which the electrode lies. This maximizes the likelihood for tissue contact while keeping the surface area within a desired range. In some embodiments, the surface area of electrode 50a is less than about 15 $mm^2$. The specifications of the electrode 50a described above are also applicable to any electrode embodiments according to the present invention, including those described below with regard to FIGS. 4-6.

Figure 4:
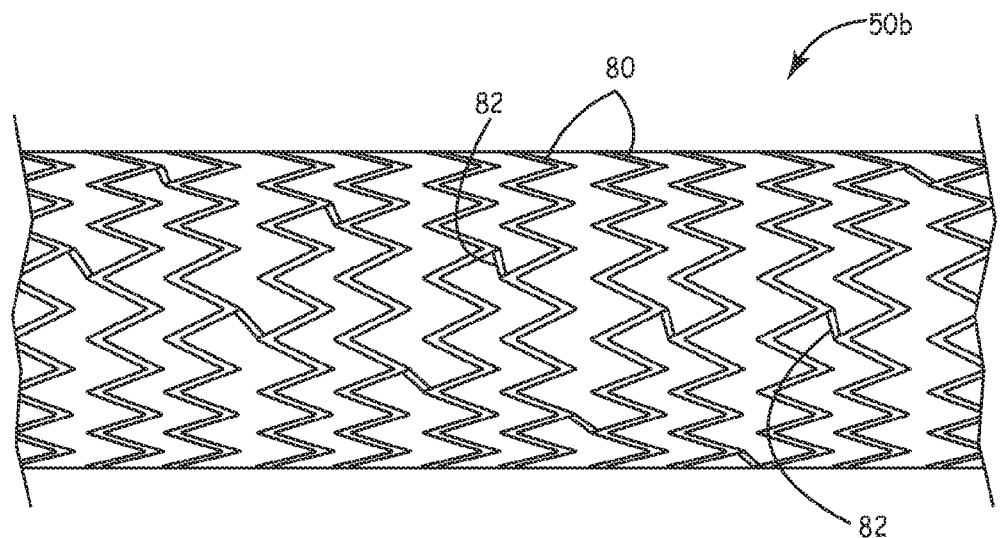
FIG. 4 is a side view of a conformal electrode according to another embodiment of the present invention.

FIG. 4 is a side view of an electrode 50b formed from a conductive tube (e.g., Nitinol) that is cut with a laser to remove material leaving behind the configuration shown. The electrode 50b includes a plurality of spaced-apart, circumferentially extending rings 80 that are connected at staggered points around the electrode 50b by struts 82 (i.e., a stent-like structure). In the embodiment shown, each of the rings 80 is comprised of a thin wire having a zigzag pattern that extends around the circumference of the electrode 50b. It will be appreciated that while a zigzag pattern is shown, the rings 80 may be alternatively formed into other circumferentially extending patterns, such as curves, loops, braids, and so on.

Figure 5:
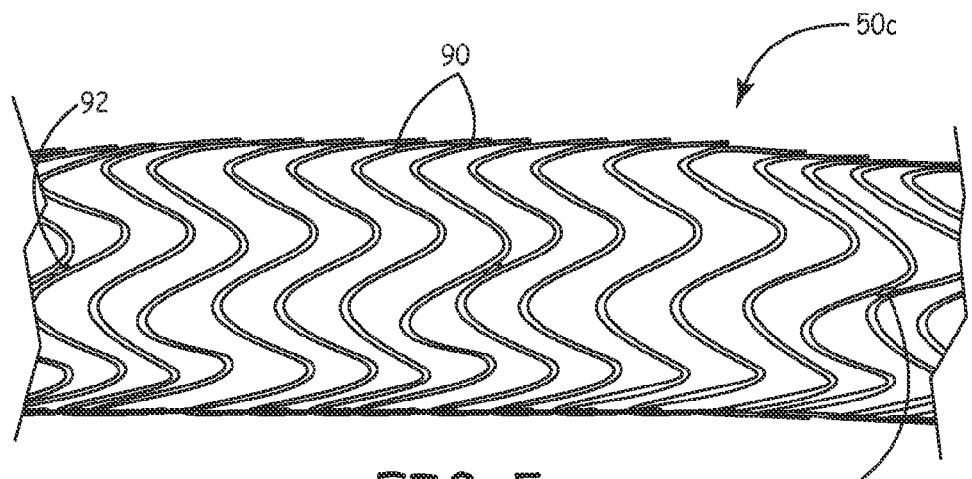
FIG. 5 is a side view of a conformal electrode according to a further embodiment of the present invention.

FIG. 5 is a side view of an electrode 50c formed from a conductive wire that has been wound into the configuration shown. The electrode 50c may be alternatively laser cut into the configuration shown from a tube of conductive material. The electrode 50c may be formed from a plurality of wire rings 90 that are individually formed into a curved shape and secured by struts or welds 92. Alternatively, the electrode 50c may be formed from a continuous length of wire that is bent into the shape shown. While the rings 90 are shown having a curved shape, it will be appreciated that other shapes are possible, including rings formed from straight lengths of wire.

Figure 6:
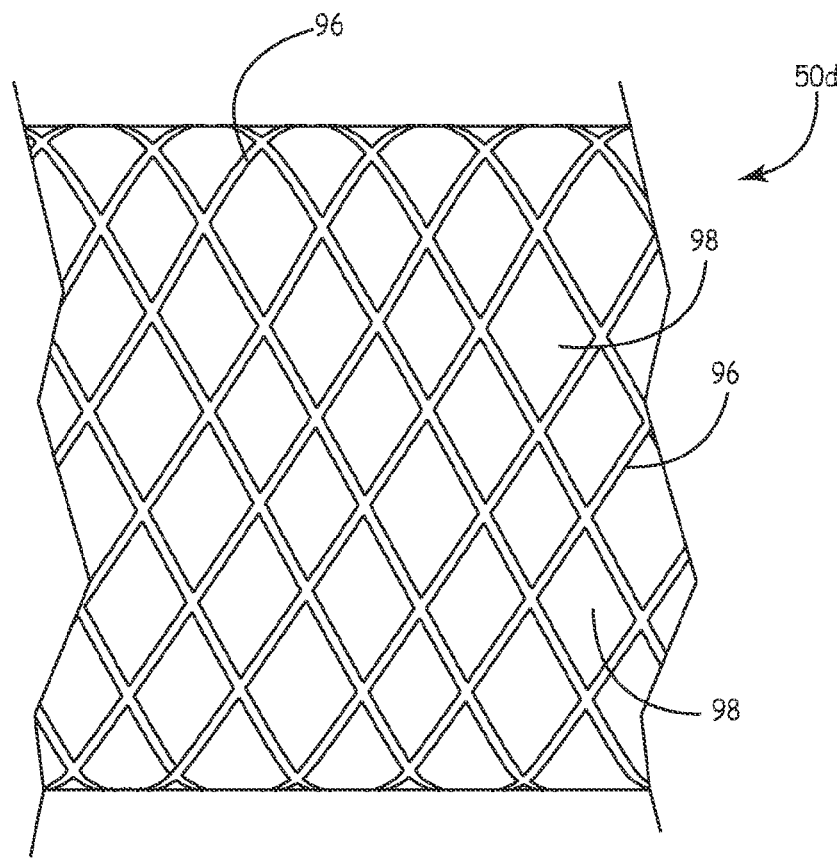
FIG. 6 is a side view of a conformal electrode according to a still further embodiment of the present invention.

FIG. 6 is a side view of an electrode 50d formed by weaving conductive wire 96 into the configuration shown. The electrode 50d may be alternatively laser cut into the configuration shown from a tube of conductive material. When the conductive wire 96 is weaved, adjacent wires can be connected to form one or more cells 98. As the number of cells 98 increases, the electrode 50d has a cage- or basket-like appearance. The conductive wire 96 can have a braided or non-braided configuration, can be spiraled, canted or arced, and can have various configurations adapted to minimize the amount of strain on the wires.

In summary, the present invention relates to a medical lead including a lead body having at least one conductor extending from a proximal end of the lead body to a distal end of the lead body. The proximal end is adapted to be connected to a pulse generator, and the distal end includes a curved portion. One or more electrodes are operatively connected to the at least one conductor and coupled to the curved portion of the lead body. At least a portion of each of the one or more electrodes includes an arrangement of interconnected, spaced-apart elements that are selectively configured to allow the one or more electrodes to conform to contours of the curved portion during and after implantation of the medical lead. The length of the electrodes can be increased, thereby improving the likelihood that the electrodes will contact tissue of the heart. At the same time, the spaced-apart elements are arranged to minimize the surface area and increase the impedance of the electrodes.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. For example, although the presented embodiments have been described in relation to leads implanted within coronary veins, it is not intended that the present invention be limited only to leads in this implant location. Shaped leads can be used in other areas of the heart, such as the atria or ventricles, or in other cardiac vessels such as the coronary arteries, pulmonary arteries or veins, and the aorta. In addition, curved lead bodies with conformal electrodes can be used for stimulation in vessels remote from the heart such as the carotid arteries or jugular veins to stimulate nerves or pressure receptors. Accordingly, the scope of the present invention is intended to embrace all such alternatives, modifications, and variations as fall within the scope of the claims, together with all equivalents thereof.

We claim:

1. A medical lead comprising:
a lead body including at least one conductor extending from a proximal end, which is adapted to be connected to a pulse generator, to a distal end, wherein the distal end comprises a preformed curved portion; and
one or more electrodes operatively connected to the at least one conductor and coupled to the preformed curved portion of the lead body, wherein at least a portion of each of the one or more electrodes includes an arrangement of interconnected, spaced-apart elements that are selectively configured to move with respect to each other such that each of the one or more electrodes is flexible and conforms to contours of the preformed curved portion during and after implantation of the medical lead, the spaced-apart elements of each electrode comprising a plurality of collars spaced apart along the longitudinal axis of the electrode and a plurality of struts, each strut extending parallel with the longitudinal axis of the electrode to connect a respective pair of adjacent collars, adjacent struts of the plurality of struts positioned in an offset arrangement with respect to each other,
wherein the spaced-apart elements have a greater surface area along portions of an exterior surface of the one or more electrodes configured to face toward tissue to be stimulated by the one or more electrodes than along portions of the exterior surface of the one or more electrodes configured to face away from the tissue to be stimulated by the one or more electrodes, and wherein an inside radius of curvature of the one or more electrodes along the preformed curved portion is comprised of less material than an outside radius of curvature of the one or more electrodes along the preformed curved portion.

2. The medical lead of claim 1, wherein the one or more electrodes are comprised of a material selected from the group consisting of NiTi, Pt, PtIr, Ti, stainless steel, and MP35N.

3. The medical lead of claim 1, wherein a surface area of each of the one or more electrodes is less than or equal to about 15 mm$^2$.

4. The medical lead of claim 1, wherein a length of each of the one or more electrodes is less than or equal to about 20 mm.

5. The medical lead of claim 4, wherein the one or more electrodes cover between about 35% and about 75% of a length of the curved portion.

6. The medical lead of claim 1, wherein the curved portion is substantially helical.

7. The medical lead of claim 6, wherein the one or more electrodes cover between about 35% and about 75% of a length of the helical portion.

8. The medical lead of claim 1, wherein the spaced-apart elements are configured to focus current density of the one or more electrodes toward tissue to be stimulated by the one or more electrodes.

9. The medical lead of claim 1, wherein the spaced-apart elements are configured to prevent movement of the one or more elements relative to tissue to be stimulated by the one or more electrodes.

10. The medical device lead of claim 1, wherein the one or more electrodes are configured to orient the electrodes toward tissue to be stimulated after implantation.

* * * * *